United States Patent
Pinsonneault

(10) Patent No.: US 9,734,541 B1
(45) Date of Patent: Aug. 15, 2017

(54) SYSTEMS AND METHODS FOR A HEALTHCARE NETWORK SURVEY SOLUTION

(75) Inventor: Roger Pinsonneault, Alpharetta, GA (US)

(73) Assignee: MCKESSON CORPORATION, San Francisco, CA (US)

( * ) Notice: Subject to any disclaimer, the term of this patent is extended or adjusted under 35 U.S.C. 154(b) by 1570 days.

(21) Appl. No.: 12/435,597

(22) Filed: May 5, 2009

(51) Int. Cl.
*G06Q 10/00* (2012.01)
*G06Q 50/22* (2012.01)

(52) U.S. Cl.
CPC .................................. *G06Q 50/22* (2013.01)

(58) Field of Classification Search
CPC .................................................... G06Q 50/22
USPC ......................................................... 705/2–3
See application file for complete search history.

(56) References Cited

U.S. PATENT DOCUMENTS

| | | | |
|---|---|---|---|
| 5,628,530 | A | 5/1997 | Thornton |
| 6,012,035 | A | 1/2000 | Freeman et al. |
| 6,757,898 | B1 | 6/2004 | Ilsen et al. |
| 6,769,228 | B1 | 8/2004 | Mahar |
| 7,155,397 | B2 | 12/2006 | Alexander et al. |
| 7,370,009 | B1 | 5/2008 | Notani et al. |
| 7,493,264 | B1 * | 2/2009 | Kelly .................. G06F 19/3431 128/903 |
| 7,734,483 | B1 | 6/2010 | Smith et al. |
| 8,719,048 | B1 | 5/2014 | Zaccaro |
| 2002/0002495 | A1 | 1/2002 | Ullman |
| 2002/0032582 | A1 * | 3/2002 | Feeney, Jr. .......... G06F 19/3462 705/2 |
| 2002/0042725 | A1 * | 4/2002 | Mayaud ............................ 705/2 |
| 2002/0087583 | A1 | 7/2002 | Morgan et al. |
| 2002/0111832 | A1 | 8/2002 | Judge |
| 2002/0184072 | A1 * | 12/2002 | Linde et al. .................... 705/10 |

(Continued)

FOREIGN PATENT DOCUMENTS

| | | |
|---|---|---|
| CA | 2482370 | 3/2006 |
| WO | 9503569 | 2/1995 |

(Continued)

OTHER PUBLICATIONS

Sampson, R.J., Taking Control of Health Care Costs, Best's Review—Life Health Insurance Edition, Nov. 1983, pp. 64-66, vol. 84, Issue 7, USA.

(Continued)

*Primary Examiner* — Elaine Gort
*Assistant Examiner* — Rajiv Raj
(74) *Attorney, Agent, or Firm* — Eversheds Sutherland (US) LLP

(57) ABSTRACT

Systems and methods are provided for a healthcare network survey solution. The systems and methods may include receiving a healthcare transaction from a remote computer, where the healthcare transaction identifies at least one of a drug, product, or service for a patient; determining that the healthcare transaction is eligible for a survey based upon an analysis of the drug, product, or service identified in the healthcare transaction request; selecting the eligible healthcare transaction for the survey based at least in part upon a random selection process; and delivering a survey request to a survey recipient associated with the healthcare transaction, where the survey request includes at least a transaction identifier for identifying the survey.

10 Claims, 10 Drawing Sheets

(56) References Cited

U.S. PATENT DOCUMENTS

| | | |
|---|---|---|
| 2002/0198831 A1 | 12/2002 | Patricelli et al. |
| 2003/0009367 A1 | 1/2003 | Morrison |
| 2003/0042298 A1* | 3/2003 | Allen et al. ............... 235/375 |
| 2003/0050799 A1 | 3/2003 | Jay et al. |
| 2003/0149625 A1 | 8/2003 | Leonardi et al. |
| 2003/0154163 A1 | 8/2003 | Phillips et al. |
| 2003/0229540 A1 | 12/2003 | Algiene |
| 2004/0039599 A1 | 2/2004 | Fralic |
| 2004/0073457 A1 | 4/2004 | Kalies |
| 2004/0078234 A1 | 4/2004 | Tallal, Jr. |
| 2004/0117323 A1 | 6/2004 | Mindala |
| 2004/0148198 A1 | 7/2004 | Kalies |
| 2004/0249745 A1 | 12/2004 | Baaren |
| 2005/0015280 A1 | 1/2005 | Gabel et al. |
| 2005/0060201 A1 | 3/2005 | Connely et al. |
| 2005/0102169 A1 | 5/2005 | Wilson |
| 2005/0154627 A1 | 7/2005 | Zuzek et al. |
| 2005/0182660 A1 | 8/2005 | Henley |
| 2005/0187793 A1 | 8/2005 | Myles |
| 2005/0197862 A1 | 9/2005 | Paterson et al. |
| 2005/0240473 A1 | 10/2005 | Ayers |
| 2005/0288972 A1 | 12/2005 | Marvin et al. |
| 2006/0020514 A1 | 1/2006 | Yered |
| 2006/0026041 A1 | 2/2006 | Ullman et al. |
| 2006/0149784 A1 | 7/2006 | Tholl et al. |
| 2006/0184391 A1 | 8/2006 | Barre et al. |
| 2006/0259363 A1 | 11/2006 | Jhetam |
| 2007/0005402 A1 | 1/2007 | Kennedy et al. |
| 2007/0033114 A1 | 2/2007 | Minor |
| 2007/0050209 A1 | 3/2007 | Yered |
| 2007/0136100 A1 | 6/2007 | Daugherty et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2008/0011844 A1 | 1/2008 | Tami |
| 2008/0172252 A1 | 7/2008 | Vovan et al. |
| 2009/0222384 A1 | 9/2009 | Rowan |

FOREIGN PATENT DOCUMENTS

| | | |
|---|---|---|
| WO | 0039737 | 7/2000 |
| WO | 2007025295 | 3/2007 |

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic: On-line Goes In-House, Chain Store Age Executive, Jan. 1987, pp. 128-32. vol. 63, Issue 1, USA.

Anonymous, TechRx Announces Successful Beta Deployment of T-Rex. PR Newswire. May 13, 2002.

Final Office Action for U.S. Appl. No. 13/436,414 mailed Jul. 30, 2015.

Non-Final Office Action for U.S. Appl. No. 13/436,414 mailed Aug. 19, 2016.

Non-Final Office Action for U.S. Appl. No. 13/436,414 mailed Dec. 3, 2014.

* cited by examiner

Examples of some survey questions:

1. Who gave you the Medication Guide for [Drug/Product]? (Select all that apply)
a) A doctor or someone in the doctor's office
b) A pharmacist or someone at the pharmacy
c) I did not get a Medication Guide for [Drug/Product]
2. Did you read the Medication Guide?
a) All
b) Most
c) Some
d) None
3. Did you understand what you read in the Medication Guide?
a) All
b) Most
c) Some
d) None
4. Did someone offer to explain to you the information in the Medication Guide?
a) Yes, my doctor or someone in my doctor's office
b) Yes, my pharmacist or someone at the pharmacy
c) No
5. Did you accept the offer?
Yes or No (If No, why)
6. Did you understand the explanation that was given to you?
a) All
b) Most
c) Some
d) None
7. Did or do you have any question about the Medication Guide?
Yes or No (If Yes, list your question below)

FIG. 8

SYSTEMS AND METHODS FOR A HEALTHCARE NETWORK SURVEY SOLUTION

FIELD OF THE INVENTION

Aspects of the invention relate generally to healthcare surveys, and more particularly, to systems and methods for identifying and surveying individuals associated with healthcare transactions of a healthcare network.

BACKGROUND OF THE INVENTION

Highly regulated drugs or products may carry significant risks to patients. Risk Evaluation & Mitigation Strategies (REMS) may be utilized to minimize the risks of the highly regulated drugs or products. However, periodic assessments of a particular REMS may be needed to determine strategy effectiveness relative to the identified goals.

A survey can be used to assess the effectiveness of a particular REMS. Current survey solutions include telephone surveys or mailed surveys. However, telephone surveys are disruptive, impersonal, and expensive. Likewise, mailed surveys are impersonal, not timely, and have a less than optimal response rate.

Pharmaceutical manufacturers supporting a REMS need a cost-effective, statistically sound method to identify and survey patients or healthcare providers about their knowledge, understanding, and healthcare practices relative to the identified goals of a REMS.

SUMMARY OF THE INVENTION

According to an example embodiment of the invention, there is a method. The method may include receiving a healthcare transaction from a remote computer, where the healthcare transaction identifies at least one of a drug, product, or service for a patient; determining that the healthcare transaction is eligible for a survey based upon an analysis of the drug, product, or service identified in the healthcare transaction request; selecting the eligible healthcare transaction for the survey based at least in part upon a random selection process; and delivering a survey request to a survey recipient associated with the healthcare transaction, where the survey request includes at least a transaction identifier for identifying the survey.

According to another example embodiment of the invention, there is a system. The system may include a memory for storing computer-executable instructions, and a processor configured to access the memory. The processor may be further configured to execute the computer-executable instructions to receive a healthcare transaction from a remote computer, where the healthcare transaction identifies at least one of a drug, product, or service for a patient; determine that the healthcare transaction is eligible for a survey based upon an analysis of the drug, product, or service identified in the healthcare transaction request; select the eligible healthcare transaction for the survey based at least in part upon a random selection process; and deliver a survey request to a survey recipient associated with the healthcare transaction, where the survey request includes at least a transaction identifier for identifying the survey.

BRIEF DESCRIPTION OF THE DRAWINGS

Reference will now be made to the accompanying drawings, which are not necessarily drawn to scale, and wherein:

FIG. 8 illustrates example survey questions, according to an example embodiment of the invention.

DETAILED DESCRIPTION

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention can provide systems and methods for identifying and surveying patients, healthcare providers, or other individuals associated with healthcare transactions of a healthcare network. According to an embodiment of the invention, example healthcare transactions may include, but are not limited to, electronic transactions used by a healthcare provider to facilitate the provision of services, services billing, and/or regulatory compliance. For example, the healthcare transactions may be associated with electronic prescription orders (e.g., an E-SCRIPT), pharmacy claims, medical claims, and/or insurance billing. If a healthcare transaction is qualified and selected for a survey, then a survey request may be provided to the patient, healthcare provider, or other recipient. The patient, healthcare provider, or other recipient can then complete a survey in accordance with the survey notification.

It will be appreciated that the surveys described herein can be used to support a Risk Evaluation & Mitigation Strategies (REMS). For example, the survey can be used to understand an individual's comprehension, knowledge, attitude, and/or behavior about a drug, product, or service. In a more particular example, the survey can also be used to determine whether a patient has received a product/medication safety guide or other safety information, and whether the patient understands the risks of the drug, product, or service. It will be appreciated that the surveys described herein can be utilized for a variety of purposes without departing from example embodiments of the invention.

System Overview

Figure 1:
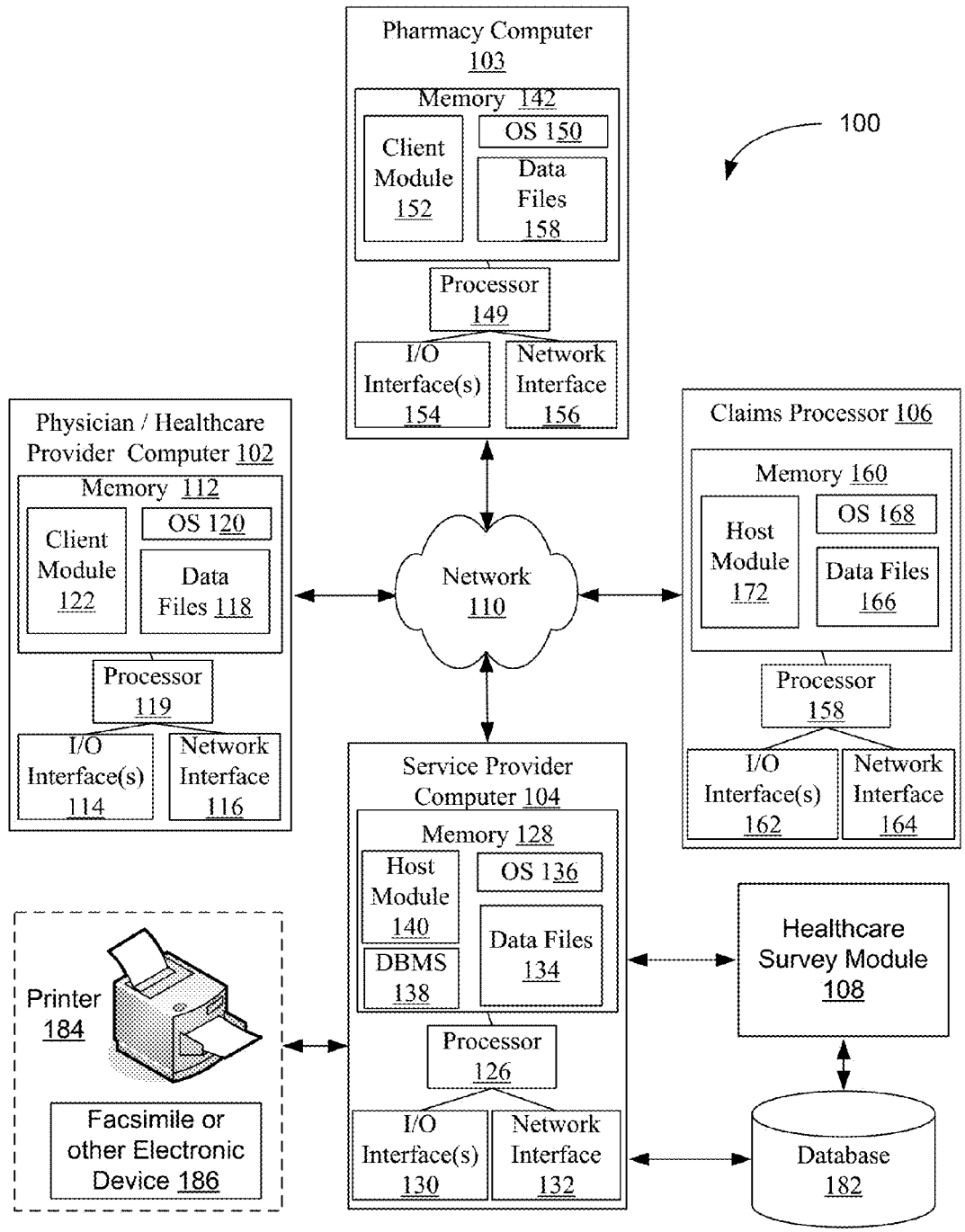
FIG. 1 illustrates an example system for identifying and surveying patients, healthcare providers, or other individuals associated with healthcare transactions of a healthcare network, according to an example embodiment of the invention.

FIG. 1 illustrates an example system 100 for identifying and surveying patients, healthcare providers (e.g., physician, pharmacist, etc.), or other individuals associated with healthcare transactions of a healthcare network, according to an example embodiment of the invention. As shown in FIG. 1, the system 100 may include a physician/healthcare provider computer 102, a pharmacy computer 103, a service provider computer 104, and a claims processor 106, which are each configured for accessing and reading associated computer-readable media having stored thereon data and/or computer-executable instructions for implementing the various methods of the invention. Generally, network devices and systems, including the one or more physician/healthcare provider computers 102, pharmacy computers 103, service provider computers 104, and claims processors 106 have hardware and/or software for transmitting and receiving data and/or computer-executable instructions over one or more communications links or networks. These network devices and systems may also include any number of processors for processing data and executing computer-executable instructions, as well as other internal and peripheral components that are well known in the art. By executing computer-executable instructions, each of the network devices may form a special purpose computer or particular machine. As used herein, the term "computer-readable medium" may describe any form of memory or memory device.

As shown in FIG. 1, the physician/healthcare provider computer 102, pharmacy computer 103, service provider computer 104, and claims processor 106 may be in communication with each other via a network 110, which as described below can include one or more separate or shared private and public networks, including the Internet or a publicly switched telephone network. Each of these components—the physician/healthcare provider computer 102, the pharmacy computer 103, the service provider computer 104, the claims processor 106, and the network 110—will now be discussed in further detail.

First, the physician/healthcare provider computer 102 may be any processor-driven device, such as, but not limited to, a personal computer, laptop computer, handheld computer, and the like. In addition to having a processor 119, the physician/healthcare provider computer 102 may further include a memory 112, input/output ("I/O") interface(s) 114, and a network interface 116. The memory 112 may be any computer-readable medium, coupled to the processor 119, such as RAM, ROM, and/or a removable storage device for storing data files 118 and a database management system ("DBMS") to facilitate management of data files 118 and other data stored in the memory 112 and/or stored in separate databases. The memory 112 may store data files 118 and various program modules, such as an operating system ("OS") 120 and a client module 122. The OS 120 may be, but is not limited to, Microsoft Windows®, Apple OSX™, Unix, or a mainframe operating system. The client module 122 may be an Internet browser or other software, including a dedicated program, for interacting with the pharmacy computer 103, the service provider computer 104, and/or the claims processor 106. For example, a physician or other healthcare provider/employee may utilize the client module 122 in preparing and providing an electronic prescription order (e.g., an E-SCRIPT for a new or refill prescription) for a patient for delivery to a designated pharmacy computer 103, according to an example embodiment of the invention.

As another example, the physician or other healthcare provider/employee may also utilize the client module 122 in preparing and providing a medical claim or insurance billing for delivery to a designated claims processor 106, according to an example embodiment of the invention. The physician or other healthcare provider may utilize the client module 122 to receive data and/or responses from the pharmacy computer 103 or service provider computer 104.

The pharmacy computer 103 may be any processor-driven device, such as a personal computer, laptop computer, handheld computer, and the like. In addition to having a processor 149, the pharmacy computer 103 may further include a memory 142, input/output ("I/O") interface(s) 154, and a network interface 156. The memory 142 may store data files 158 and various program modules, such as an operating system ("OS") 150 and a client module 152. The memory 142 may be any computer-readable medium, coupled to the processor 149, such as RAM, ROM, and/or a removable storage device for storing data files 158 and a database management system ("DBMS") to facilitate management of data files 158 and other data stored in the memory 142 and/or stored in separate databases. The OS 150 may be, but is not limited to, Microsoft Windows®, Apple OSX™, Unix, or a mainframe operating system. The client module 152 may be an Internet browser or other software, including a dedicated program, for interacting with the physician/healthcare provider computer 102, the service provider computer 104, and/or the claims processor 106. For example, a user such as a pharmacist or other pharmacy employee may utilize the client module 152 to receive or retrieve an electronic prescription order from the physician/healthcare provider computer 102. Likewise, the pharmacist or other pharmacy employee may also utilize the client module 152 in preparing and providing a prescription claim to the service provider computer 104 for delivery to the appropriate claims processor 106. The pharmacy computer 103 may also utilize the client module 152 to retrieve or otherwise receive data or responses from the service provider computer 104.

The service provider computer 104 may include, but is not limited to, any processor-driven device that is configured for receiving, processing, and fulfilling requests from the physician/healthcare provider computer 102, pharmacy computer 103, and/or claims processor 106, relating to prescription, pharmacy, benefits, and/or claim transactions or other activities. According to an example embodiment of the invention, the service provider computer 104 may comprise, but is not limited, to one or more "switches" or "switch providers" performing routing and processing of healthcare transactions between healthcare providers, pharmacies, payors/claims processors, and/or other service providers.

The service provider computer 104 may include a processor 126, a memory 128, input/output ("I/O") interface(s) 130, and a network interface 132. The memory 128 may be any computer-readable medium, coupled to the processor 126, such as RAM, ROM, and/or a removable storage device for storing data files 134 and a database management system ("DBMS") 138 to facilitate management of data files 134 and other data stored in the memory 128 and/or stored in one or more databases 144. The memory 128 may store data files 134 and various program modules, such as an operating system ("OS") 136, a database management system ("DBMS") 138, and the host module 140. The OS 136 may be, but is not limited to, Microsoft Windows®, Apple OSX™, Unix, or a mainframe operating system.

The data files 134 may also store routing tables for determining the destination of communications received from the physician/healthcare provider computer 102, pharmacy computer 103, or claims processor 106. The host module 140 may receive, process, and respond to requests from the respective client modules 122, 152 of the physician/healthcare provider computer 102 or pharmacy computer 103, and may further receive, process, and respond to requests from the host module 172 of the claims processor 106. The database 182 may be one or more databases operable for storing information utilized in qualifying and/or selecting patients or healthcare providers for surveys.

As also illustrated in FIG. 1, the service provider computer 104 may include or otherwise be in communication with a healthcare survey module 108. The healthcare survey module 108 may include business rules, perhaps stored in a data storage device 182, for qualifying and/or selecting a healthcare transaction for one or more surveys. If a healthcare transaction is qualified and/or selected, the healthcare survey module 108, either alone or in conjunction with the service provider computer 104, may direct the transmission of a survey request to a printer 184 or facsimile/other electronic device 186, which may be at or near a healthcare provider location of a physician or pharmacist. However, it will be appreciated that the printer 184 or facsimile/other electronic device 186 may also be at another location or associated with another individual (e.g., the patient) or entity without departing from example embodiments of the invention. The transmission of the survey request from the healthcare survey module 108 to the printer 184 or facsimile/other electronic device 186 may be accomplished via any number of suitable networks, for example, a telephone network, a local area network, a wide area network, a cellular network, a wireless network, the Internet, or another similar network. The healthcare survey module 108 may also be implemented as computer-implemented instructions of the memory 128 of the service provider computer 104. Alternatively, the healthcare survey module 108 may also be implemented as computer-implemented instructions of a memory of separate processor-based system that operations in tandem with the service provider computer 104, according to an example embodiment of the invention. It will be appreciated that while the service provider computer 104 has been illustrated as a single computer or processor, the service provider computer 104 may be comprised of a group of computers or processors, according to an example embodiment of the invention.

The claims processor 106 may be any processor-driven device that is configured for performing benefits determination and/or adjudication of healthcare claim requests. The claims processor 106 may include a processor 158, a memory 160, input/output ("I/O") interface(s) 162, and a network interface 164. The memory 160 may be any computer-readable medium, coupled to the processor 158, such as RAM, ROM, and/or a removable storage device for storing data files 166 and a database management system ("DBMS") to facilitate management of data files 166 and other data stored in the memory 160 and/or stored in separate databases. The memory 160 may store data files 166 and various program modules, such as an operating system ("OS") 168, a database management system ("DBMS"), and a host module 172. The OS 168 may be, but is not limited to, Microsoft Windows®, Apple OSX™, Unix, or a mainframe operating system. The host module 172 may receive, process, and respond to requests from the client module 122 of the physician/healthcare provider computer 102 or client module 152 of the pharmacy computer 103, and may further receive, process, and respond to requests from the host module 140 of the service provider computer 104. According to an example embodiment of the invention, the claims processor 106 may be associated with benefits determination by a discount program, an insurance company, a pharmacy benefits manger (PBM), a government payor, or another third-party payor. According to an alternative example embodiment of the invention, a claims processor 106 may also be implemented as part of a service provider computer 104.

The network 110 may include any telecommunication and/or data network, whether public, private, or a combination thereof, including a local area network, a wide area network, an intranet, an internet, the Internet, intermediate hand-held data transfer devices, a publicly switched telephone network (PSTN), and/or any combination thereof and may be wired and/or wireless. The network 110 may also allow for real-time, off-line, and/or batch transactions to be transmitted between or among the physician/healthcare provider computer 102, the pharmacy computer 103, or the service provider computer 104. Due to network connectivity, various methodologies as described herein may be practiced in the context of distributed computing environments. It will also be appreciated that the network 110 may include a plurality of networks, each with devices such as gateways and routers for providing connectivity between or among networks 110. Instead of or in addition to a network 110, dedicated communication links may be used to connect the various devices in accordance with an example embodiment of the invention. For example, the service provider computer 104 may form the basis of network 110 that interconnects the physician/healthcare provider computer 102 with the pharmacy computer 103, or that interconnects the pharmacy computer 103 with the claims processor 106.

The system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. As another example, in one example embodiment, the service provider computer 104 (or the physician/healthcare provider computer 102/claims processor 106) may be implemented as a specialized processing machine that includes hardware and/or software for performing the methods described herein. In addition, the processor and/or processing capabilities of the service provider computer 104 and/or the healthcare survey module 108, may be implemented as part of the physician/healthcare provider computer 102, the pharmacy computer 103, the claims processor 106, or any combination or portion thereof. Accordingly, embodiments of the invention should not be construed as being limited to any particular operating environment, system architecture, or device configuration.

Operational Overview

A. Electronic Prescription Order Transaction

Figure 2A:
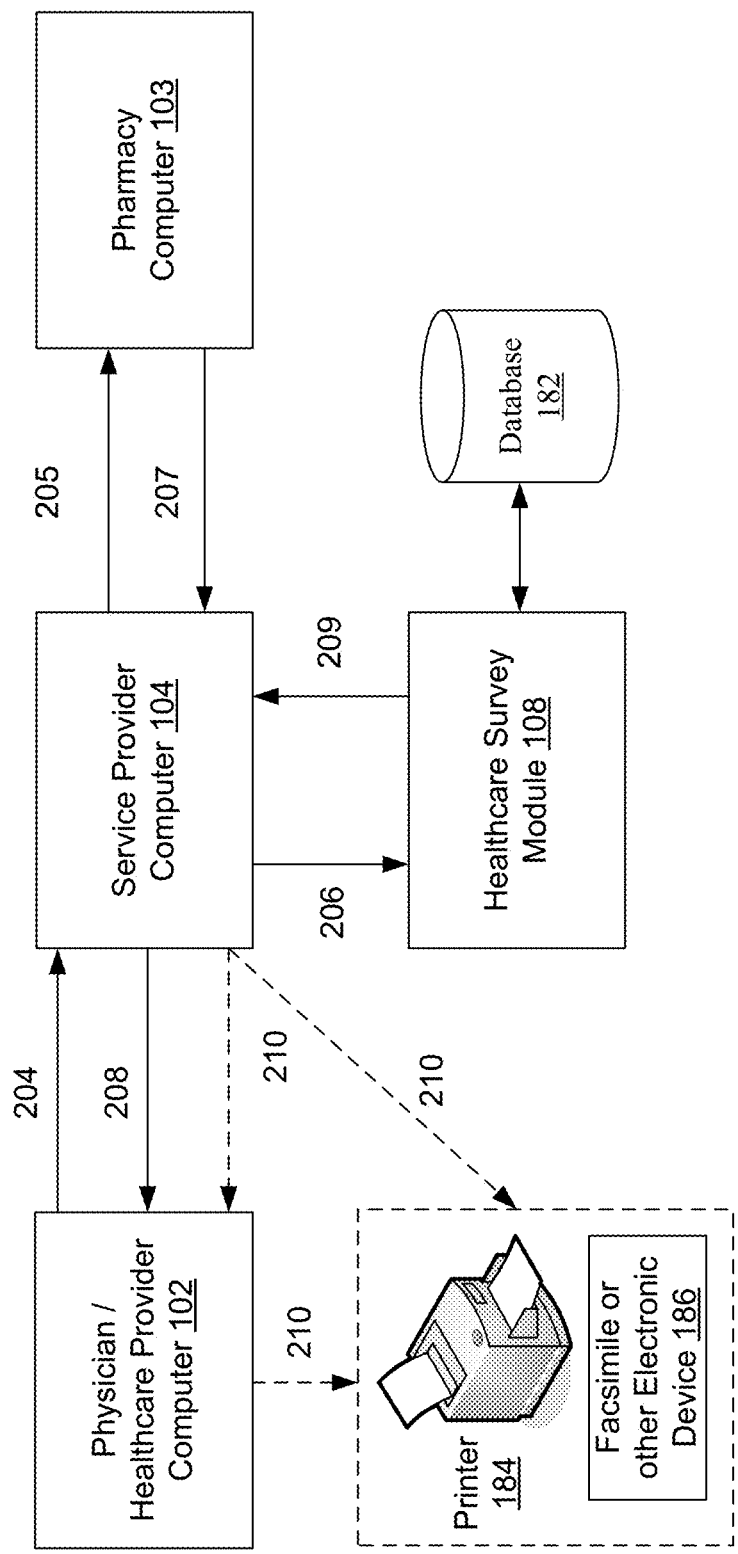
FIGS. 2A and 2B illustrate example block diagrams for providing a survey request based upon an electronic prescription order transaction, according to an example embodiment of the invention.
Figure 3:
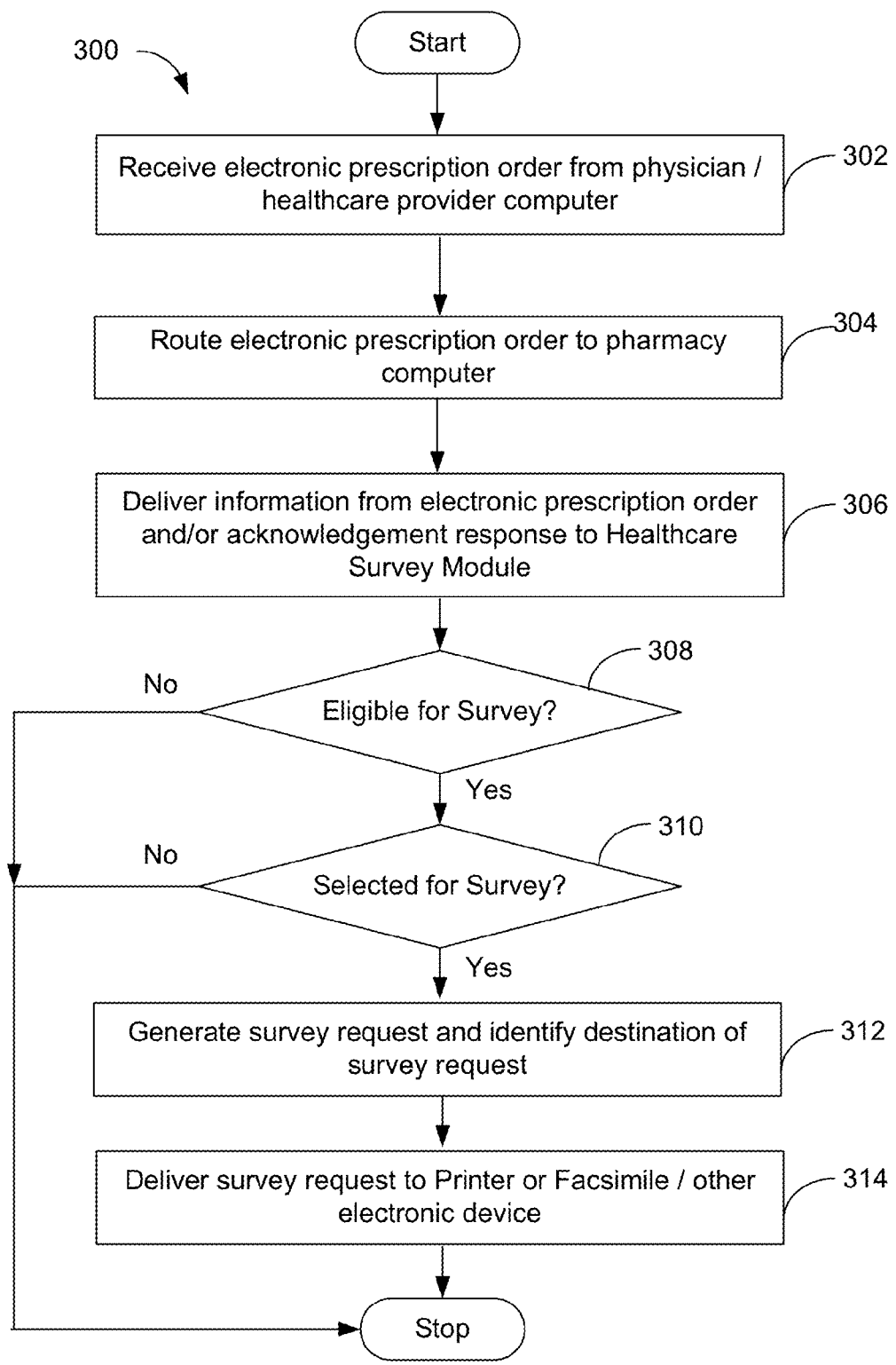
FIG. 3 illustrates an example flow diagram for providing a survey request based upon an electronic prescription order transaction, according to an example embodiment of the invention.

FIGS. 2A and 3 illustrate a respective block diagram and flow diagram 300 for providing a survey request based upon an electronic prescription order transaction, according to an example embodiment of the invention.

Referring now to FIGS. 2A and 3, in block 302, a physician/healthcare provider computer 102 may deliver or otherwise communicate a healthcare transaction request in the form of an electronic prescription order 204 to a service provider computer 104. Accordingly, the service provider computer 104 may receive an electronic prescription order 204 in block 302. According to an example embodiment of the invention, the electronic prescription order 204 may be in the form of a new prescription script (e.g., a NEWRX transaction) or a refill prescription script (e.g., a REFRES transaction), although other formats may be utilized as well. The electronic prescription order 204 may be destined for a designated pharmacy computer 103 and may include a corresponding pharmacy identifier. The electronic prescription order 204 may also include information relating to the physician/healthcare provider, the prescribed drug or product, diagnosis/ailment information, and/or the patient. For example, physician/healthcare provider information may include a name, contact information (e.g., address, zip code, and/or telephone number), and/or an identifier for the prescribing physician (e.g., a National Provider Identifier (NPI) code or Drug Enforcement Administration (DEA) number). The prescribed drug or product information may include a name of a prescribed drug or product, a drug/product identifier (e.g., a National Drug Code (NDC), UPC number), or other information such as quantity, refills, form (e.g., tablet, gel, etc.), dosage instructions, and/or date for the prescription. The diagnosis/ailment information may include certain codes or identifiers to identify the condition(s) that the drug or product is being prescribed to treat. The patient information may include a name, contact, and/or location information for the patient, as well as other patient information such as a date of birth (DOB) or gender code/information.

In block 304, the service provider computer 104 may route or deliver a copy of the electronic prescription order 204 to the designated pharmacy computer 103 as electronic prescription order 205. The pharmacy computer 103 may provide a response 207 to the service provider computer 104. The response 207 may also be delivered by the service provider computer 104 to the physician/healthcare provider computer 102 as a response 208. The response 208 may indicate whether the pharmacy has successfully received the electronic prescription order 205.

In block 306, the service provider computer 104 may also deliver a copy of the electronic prescription order 204 and/or response 207 to the healthcare survey module 108 in one or more messages 206. For multiple deliveries, the service provider computer 104 may have initially provided a copy of the electronic prescription order 204 according to a first delivery at a first time, and then provided a copy of the response 207 according to a second delivery at a second time. Where the healthcare survey module 108 is part of the service provider computer 104, the delivery of the one or more messages 206 may be an internal delivery or an intra-network delivery. However, where the healthcare survey module 108 is distinct from the service provider computer 104, then the delivery of the one or more messages 206 may be an external delivery or inter-network delivery, perhaps via a network 110, according to an example embodiment of the invention. In block 306, the healthcare survey module 108 may parse or examine the copy of the electronic prescription order 204 and/or acknowledgement response 207 received in the one or more messages 206 to obtain information for use in identifying and/or selecting potential survey candidates. Example information that may be obtained by the healthcare survey module 108 from the electronic prescription order 204 or response 207 may include a prescribed drug or product identifier (e.g., NDC, UPC, etc.), a name of the prescribed drug or product, physician/healthcare provider identification information (e.g., DEA number or NPI code, etc.), pharmacy identification information (e.g., NPI code, pharmacy name, etc.), patient information (e.g., gender code, date of birth, location information, etc.), and/or transaction response (e.g., prescription order successfully accepted by pharmacy computer).

In block 308, the healthcare survey module 108 may determine whether the electronic prescription order transaction is eligible as a potential survey candidate. In an example embodiment, the eligibility requirements may be determined or provided by a sponsor of the survey, which may, for example, be a manufacturer of the drug or product identified by the electronic prescription order transaction. The eligibility requirements may be based upon a prescribed drug or product identifier (e.g., NDC, UPC, etc.) received in the one or more messages 206. As an example, block 308 may utilize the drug or product identifier to determine whether the electronic prescription order transaction involves a particular drug or product that is the subject of a particular survey.

Other eligibility requirements for block 308 may be based upon an analysis of additional information received in the one or more messages 206, including, but not limited to: (i) gender code/information of the patient, (ii) patient date of birth, (iii) patient zip code or other location information, and/or (iv) transaction response (e.g., acknowledgement response indicating successful receipt of prescription order by pharmacy computer). As an example, block 308 may utilize the gender information/code if the survey is targeted towards patients of a particular gender (e.g., female or male). Similarly, block 308 may utilize the Date of Birth if the survey is targeted towards patients of a particular age or age range (e.g., seniors over 65 years old). The patient zip code or other location information may be utilized by block 308 if the survey is targeted towards patients residing in a particular geographical location. The transaction response may be utilized by block 308 to ensure that the survey is provided based upon successful electronic prescription orders. It will be appreciated that additional or alternative eligibility requirements may also be utilized in block 308 without departing from example embodiments of the invention. In addition, external information, perhaps stored in database 182, may also be utilized for the eligibility requirements of block 308. As an example, the survey may be targeted towards prescribers having a particular specialty. In this case, the prescriber identifier received in the one or more messages 206, may be compared to an external physician specialty code listing, perhaps stored in database 182, that identifies prescribers of a particular specialty.

If block 308 determines that the electronic prescription order transaction is eligible as a potential survey candidate, then processing may proceed to block 310. Block 310 may determine whether the potential survey candidate should actually be selected for the survey. In an example embodiment of the invention, block 310 may select the potential survey candidate based upon a result of one or more random selection processes. The random selection processes may be utilized to ensure that the survey sample is statistically sound (e.g., properly distributed sample). It will be appreciated that block 310 may select the potential survey candidate based upon other selection processes as well. For example, if a survey sponsor wishes to select 10% of all potential survey candidates for an actual survey, then block 310 could simply select every tenth potential survey candidate that is identified for the particular survey.

If block 310 determines that the potential survey candidate should actually be selected for the survey, then processing may proceed to block 312. In block 312, the healthcare survey module may generate a survey request and identify a destination of the survey request. The survey request may provide instructions that describe how the survey recipient can access the particular survey (e.g., an Internet address for a network portal/website or a telephone number of a call center/interactive voice response (IVR) system. Alternatively, the survey request may otherwise include one or more survey questions to be completed by the recipient. In addition, the survey request may also include a transaction ID or survey ID for use in subsequently accessing a particular survey corresponding to the transaction ID or survey ID. In an example embodiment of the invention, the transaction ID or survey ID may be a unique identifier for each healthcare transaction. For example, the transaction ID or survey ID may correspond not only to a particular survey, but also a particular healthcare transaction. Block 312 may also identify the destination of the survey request by accessing a provider list, which may be stored in database 182 or another storage location. In particular, a provider list may allow block 312 to match physician/healthcare provider information or ID (e.g., NDC, NPI, etc.) received in the one or more messages 206 to the corresponding information of an entry in the provider list, as illustratively provided in Table I below. The matching entry may provide the delivery type and Destination ID associated with the Delivery Type. For example, for a Facsimile Delivery Type, the Destination ID may include a telephone number associated with the facsimile. As another example, for a Printer Delivery Type, the Destination ID may include a Printer ID or a Network ID corresponding to the printer.

TABLE I

| Healthcare Provider/ Pharmacy Name | Healthcare Provider/ Pharmacy Information or ID (e.g., NPI or DEA) | Healthcare Provider/ Pharmacy Contact Information (e.g., address, phone number) | Delivery Type | Destination ID |
|---|---|---|---|---|
| Physician or Pharmacy Name #1 | DEA #1 | Address & Phone Number | Facsimile | Fax Number |
| Physician or Pharmacy Name #2 | NPI #2 | Address & Phone Number | Printer | Printer ID |
| ... | ... | ... | ... | ... |

Still referring to block 312, the healthcare survey module 108 may deliver a response 209 to the service provider computer 104. The response 209 may include the survey request and identification of the destination of the survey request (e.g., Destination Type, Destination ID). In an example embodiment of the invention, the destination of the survey request may designate a particular printer 184 or facsimile/other electronic device 186.

In block 314, the service provider computer 104 may deliver a message 210 with the survey request to the designated printer 184 or facsimile/other electronic device 186. In an example embodiment of the invention, the service provider computer 104 may direct the delivery of the message 210 with the survey request to the printer 184 or facsimile/other electronic device 186 via one or more networks, including the Internet, a cellular network or other wireless network, or a telephone network. As an example, the message 210 having the survey request may be delivered to the printer 184 or facsimile/other electronic device 186 without first being received by the physician/healthcare provider computer 102. For example, the message 210 may be delivered via a network (e.g., a cellular network, telephone network) using the destination ID (e.g., Network/ Printer ID, telephone number, etc.) corresponding to the printer 184 or facsimile/other electronic device 186. According to another example, the message 210 having the survey request may be delivered from the service provider computer 104 to the physician/healthcare provider computer 102 (e.g., as part of or distinct from the response 208), which in turn may deliver the message 210 having the survey request to the printer 184 or facsimile/other electronic device 186, which may be located at the physician/healthcare provider location. In an example embodiment of the invention, the message 210 may also provide a notification to the physician/healthcare provider computer 102 that the healthcare/ informational content has been delivered to the printer 184 or facsimile/other electronic device 186. If the patient is the intended recipient of the survey request, then the patient may be provided with the survey request.

Figure 2B:
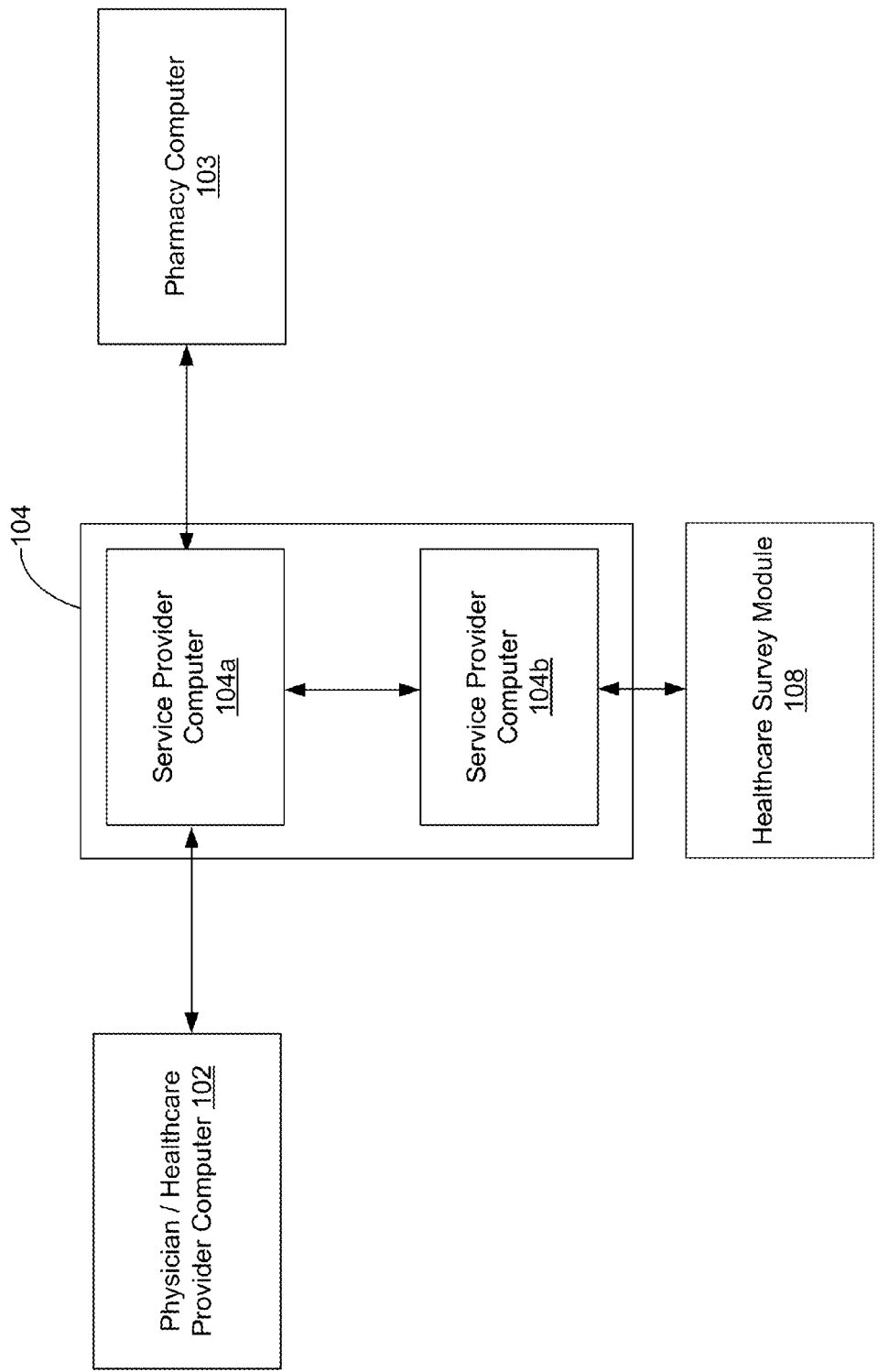

FIG. 2B illustrates a variation of the block diagram of FIG. 2A. As shown by FIG. 2B, the service provider computer 104 may be comprised of two or more distinct service provider computers 104a and 104b that are in communication with each other. Service provider computer 104a may be operative with the physician/healthcare provider computer 102 and pharmacy computer 103 while service provider computer 104b may be operative with other physician/healthcare provider computers and/or pharmacy computers. However, service provider computer 104b may have a data processing arrangement with service provider computer 104a. Under the data processing agreement, the service provider computer 104a may be permitted to utilize or offer services of the service provider computer 104b, including the services of the healthcare survey module 108. Accordingly, the services accessible by the service provider computer 104b, including the services of the healthcare survey module 108, may be available to the pharmacy computer 103 via the service provider computers 104a and 104b.

It will also be appreciated that variations of FIG. 3 are also available without departing from example embodiments of the invention. According to a variation of FIG. 3, the service provider 104 may not automatically route the electronic prescription order to the pharmacy computer 103, as provided in block 304. Instead, if block 308/310 determines that the particular electronic prescription order transaction will not be selected for the survey, then the service provider 104 can proceed to perform the routing of block 304. However, if block 308/310 determines that the particular electronic prescription order transaction is indeed being selected for the survey, then the service provider 104 will deliver a denial response with a message to the physician/healthcare provider computer 102. The message may indicate that a survey request is being submitted to a printer 184 or facsimile/other electronic device 186, and should be delivered to a particular recipient. The message may further request the physician/ healthcare provider computer 102 resubmit the electronic prescription order transaction, perhaps with a particular override code, so that the service provider 104 can complete the electronic prescription order transaction by routing the transaction to the pharmacy computer 103. The above-described denial and resubmission process may increase the probability that the survey request reaches the intended recipient.

It will also be appreciated that according to other example embodiments of the invention, a service provider computer 104 may also direct a paper mailing of the survey request, including any survey questions, to a physical address of the intended recipient. The recipient can then mail the completed survey to a return location, or may otherwise use one of the other methods (e.g., network portal/website, call center, IVR system, etc.) described herein.

B. Healthcare Claim Transaction

Figure 4A:
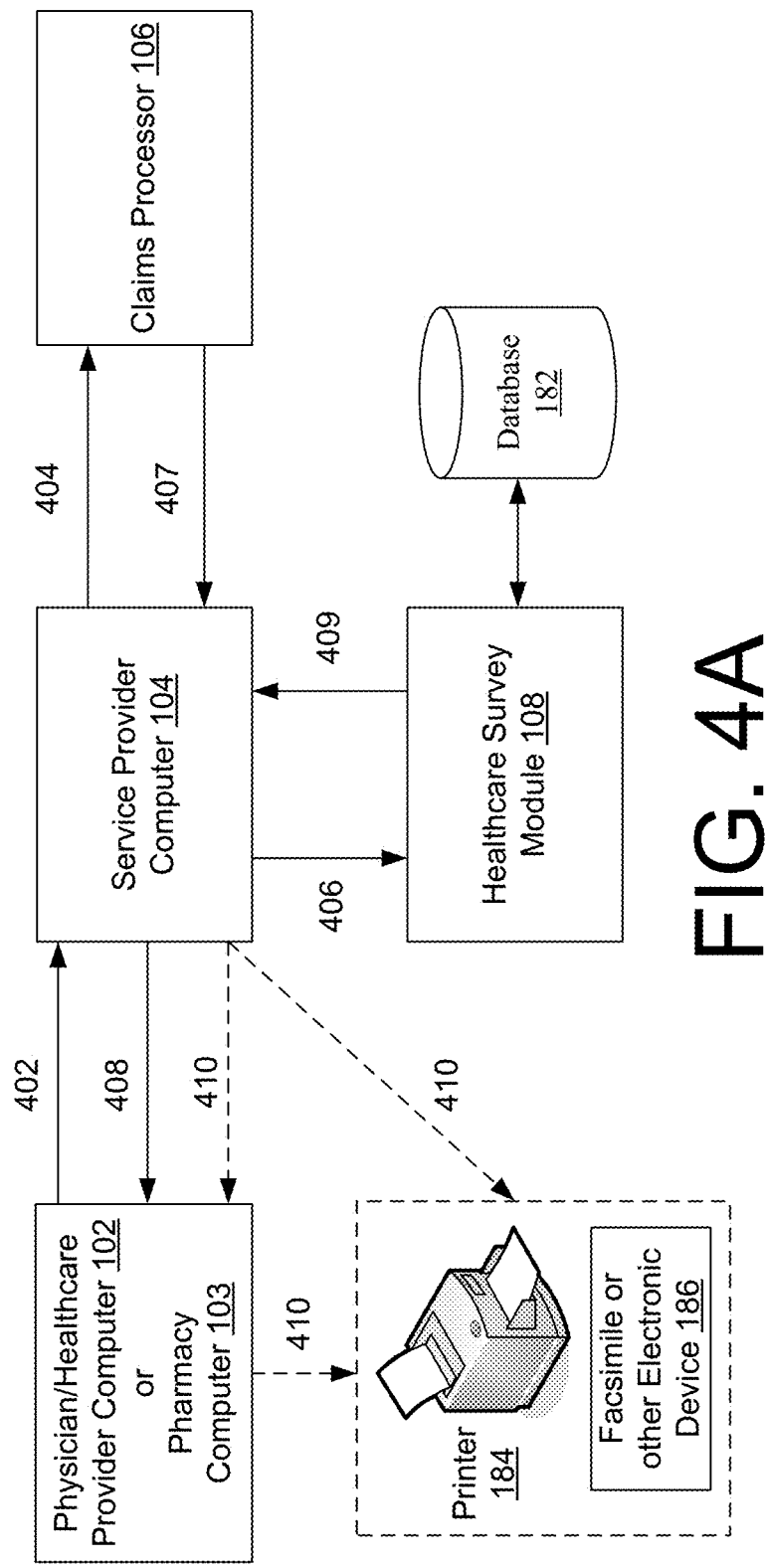
FIGS. 4A and 4B illustrate example block diagrams for providing a survey request based upon a healthcare claim transaction, according to an example embodiment of the invention.
Figure 5:
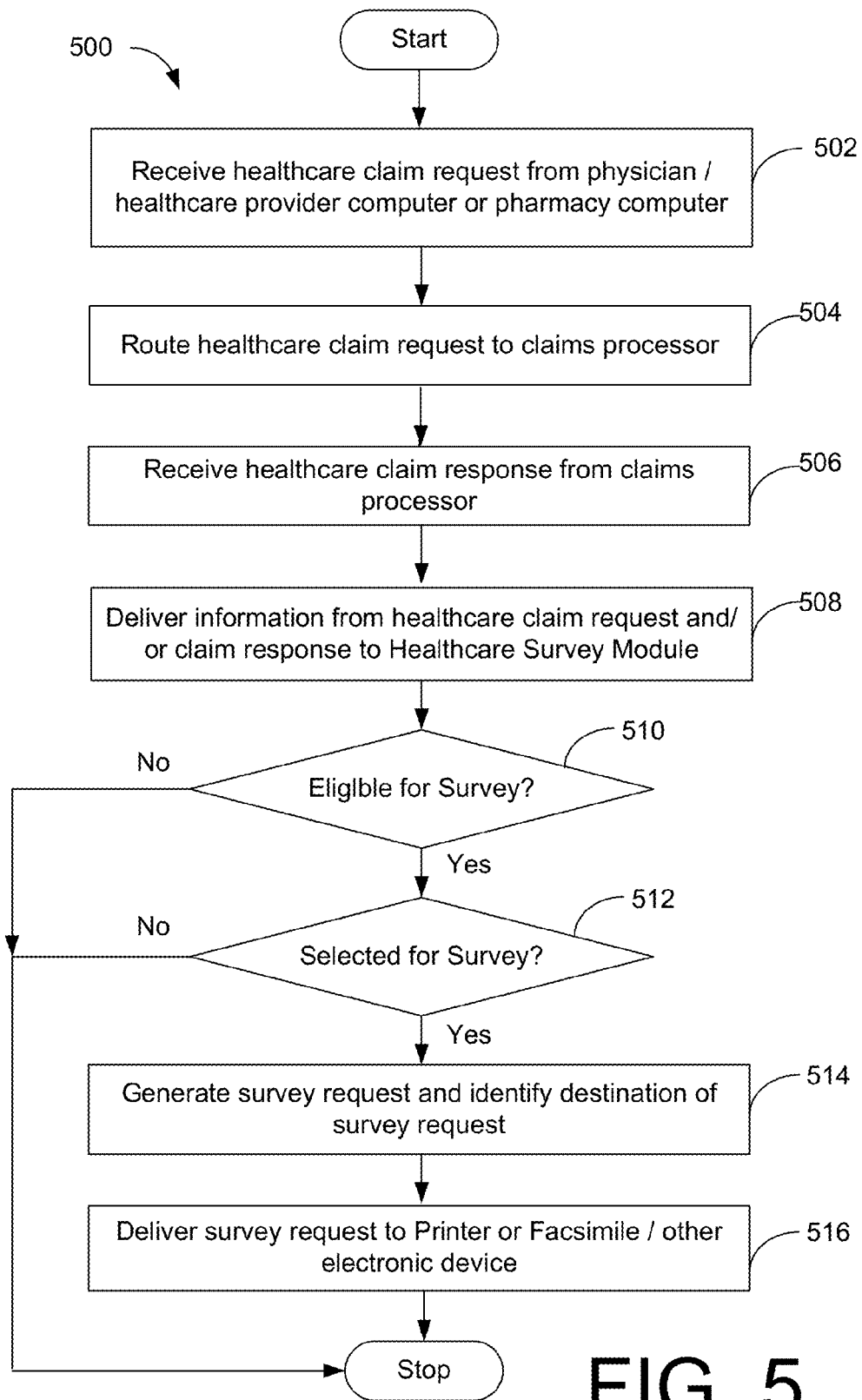
FIG. 5 illustrates an example flow diagram for providing a survey request based upon a healthcare claim transaction, according to an example embodiment of the invention.

FIGS. 4A and 5 illustrate a respective block diagram and flow diagram 500 for providing a survey request based upon a healthcare claim transaction, according to an example embodiment of the invention.

Referring now to FIGS. 4A and 5, in block 502, a physician/healthcare provider computer 102 or a pharmacy computer 103 may deliver or otherwise communicate a healthcare claim request 402 to the service provider computer 104. Accordingly, the service provider computer 104 may receive the healthcare claim request 402 in block 502. The healthcare claim request 402 may include information relating to the patient, healthcare provider, payer, and provided drug/product or service. As an example, the healthcare claim request 402 received by the service provider computer 104 may include one or more of the following information:

Patient information, including a name/identifier, contact, and/or location information, as well as a date of birth (DOB) or gender code/information, a Banking Identification Number (BIN) and/or a Processor Control Number (PCN) associated with a designated claims processor 106, an identification of the drug/product (e.g., National Drug Code (NDC), UPC) or service provided to the patient, a diagnosis/condition associated with the patient, a healthcare provider identifier (e.g., National Provider Identifier (NPI) code, Drug Enforcement Administration (DEA) number, state-issued identification, etc.), and/or a date of service.

In an example embodiment of the invention, the healthcare claim request 402 may be a medical claim request generated by a physician/healthcare provider computer 102 that is associated with a medical office such as a physician office, a clinic, or a hospital. The medical claim request may identify a service, drug, or product provided for the patient. Likewise, the medical claim request may also identify an ailment/condition associated with the patient. The healthcare provider identifier (e.g., NPI code, DEA number, etc.) in the medical claim request may identify the physician or other healthcare provider providing the service or product to the patient. According to an example embodiment of the invention, a medical claim request may be in an ASC X12N 837 format, although other formats may be accepted by the service provider computer 104 as well.

On the other hand, the healthcare claim request 402 may be a prescription claim request generated by a pharmacy computer 103 that is associated with a pharmacy location. The prescription claim request may identify (e.g., by NDC or other drug/product identifier) a prescribed drug or product that is to be filled for the patient by the pharmacy. The healthcare provider identifier (e.g., NPI code, DEA number, etc.) in the prescription claim request may identify the physician or other healthcare provider that prescribed the drug or product that is to be filled for the patient by the pharmacy. According to an example embodiment of the invention, the pharmacy claim request may be in accordance with a version of an NCPDP Telecommunication Standard, although other formats may be accepted by the service provider computer 104 as well.

In block 504, the service provider computer 104 may determine the destination claims processor 106 based upon a BIN/PCN included with the healthcare claim request 402. The service provider computer 104 may then route or deliver a copy of the healthcare claim request 402 to the destination claims processor 106 as healthcare claim request 404 for coverage or benefits determination by a discount program, insurance company, pharmacy benefits manager (PBM), government payor, or another third-party payor. Where the claims processor 106 is implemented as part of the service provider computer 104, the delivery of the healthcare claim request 404 may be an internal delivery or intra-network delivery. However, where the claims processor 106 is distinct from the service provider computer 104, the delivery of the healthcare claim request 404 may be an external delivery or inter-network delivery, perhaps via a network 110, according to an example embodiment of the invention.

In block 506, the claims processor 106 may adjudicate the healthcare claim request 404 and generate a claim response 407. The claim response 407 may specify a paid/covered amount (e.g., an insured amount) and a patient-responsible amount (e.g., a co-pay or coinsurance amount). Alternatively, the claim response 407 may indicate a denial of coverage for the healthcare claim request 404. In block 506, the claims processor 106 may then deliver the claim response 407 to the service provider computer 104. The claim response 407 may also be provided to the originating physician/healthcare provider computer 102 or pharmacy computer 103 as claim response 408.

In block 508, the service provider computer 104 may also deliver a copy of the healthcare claim request 402 and/or claim response 407 to the healthcare survey module 108 in one or more messages 406. For multiple deliveries, the service provider may have initially provided a copy of the healthcare claim request 402 according to a first delivery at a first time, and then provided a copy of the claim response 407 according to a second delivery at a second time. Where the healthcare survey module 108 is part of the service provider computer 104, the delivery of the one or more messages 406 may be an internal delivery or an intra-network delivery. However, where the healthcare survey module 108 is distinct from the service provider computer 104, then the delivery of the one or more messages 406 may be an external delivery or inter-network delivery, perhaps via a network 110, according to an example embodiment of the invention.

Still referring to block 508, the healthcare survey module 108 may parse or examine the copy of the healthcare claim request 402 and/or claim response 407 received in the one or more messages 406 to obtain information for use in identifying and/or selecting potential survey candidates. Example information that may be obtained by the healthcare survey module 108 from the healthcare claim request 402 may include an identification of the provided drug/product (e.g., NDC, UPC, HRI, etc.) or service, condition/ailment information associated with the patient, physician identification information (e.g., DEA number or NPI code, etc.), and/or patient information (e.g., gender code, date of birth, location information, etc.).

In block 510, the healthcare survey module 108 may determine whether the healthcare claim transaction is eligible as a potential survey candidate. In an example embodiment, the eligibility requirements may be determined or provided by a sponsor of the survey, which may, for example, be a manufacturer of the drug or product or provider of a service identified by the healthcare claim transaction. The eligibility requirements may be based upon a drug/product identifier (e.g., NDC, UPC, HRI, etc.) or service identifier received in the one or more messages 406. As an example, block 510 may utilize the drug/product identifier or service identifier to determine whether the healthcare claim transaction involves a particular drug, product, or service that is the subject of a particular survey.

Other eligibility requirements for block 510 may be based upon an analysis of additional information received in the one or more messages 406, including, but not limited to: (i) gender information/code of the patient, (ii) patient date of birth, (iii) patient zip code or other location information, and/or (iv) transaction response (e.g., Paid Claim). As an example, block 510 may utilize the gender information/code if the survey is targeted towards patients of a particular gender. Similarly, block 510 may utilize the patient date of birth if the survey is targeted towards patients of a particular age or age range (e.g., seniors over 65 years old). The patient zip code or other location information may be utilized by block 510 if the survey is targeted towards patients residing in a particular geographical location. The transaction response may be utilized by block 510 to ensure that the survey is provided based upon approved or paid healthcare claims. It will be appreciated that additional or alternative eligibility requirements may also be utilized in block 510 without departing from example embodiments of the invention. In addition, external information, perhaps stored in database 182, may also be utilized for the eligibility requirements of block 510. As an example, the survey may be targeted towards healthcare providers having a particular specialty. In this case, the healthcare provider identifier received in the one or more messages 406, may be compared to an external provider specialty code listing, perhaps stored in a database 182, that identifies providers of a particular specialty.

If block 510 determines that the healthcare claim transaction is eligible as a potential survey candidate, then processing may proceed to block 512. Block 512 may determine whether the potential survey candidate should actually be selected for the survey. In an example embodiment of the invention, block 512 may select the potential survey candidate based upon a result of one or more random selection processes. The random selection processes may be utilized to ensure that the survey sample is statistically sound. It will be appreciated that block 512 may select the potential survey candidate based upon other processes as well. For example, if a survey sponsor wishes to survey 10% of all potential survey candidates, then block 512 could simply select every tenth potential survey candidate that is identified for the particular survey.

If block 512 determines that the potential survey candidate should actually be selected for the survey, then processing may proceed to block 514. In block 514, the healthcare survey module may generate a survey request and identify a destination of the survey request. The survey request may provide instructions that describe how the survey recipient can access the particular survey. Alternatively, the survey request may also include one or more survey questions to be completed by the recipient. In addition, the survey request may also include a transaction ID or survey ID for use in subsequently accessing a particular survey corresponding to the transaction ID or survey ID. Block 514 may also identify the destination of the survey request by accessing a provider list, which may be stored in database 182 or another storage location. In particular, a provider list may allow block 514 to match physician/healthcare provider information or ID (e.g., NDC, NPI, etc.) received in the one or more messages 406 to the corresponding information of an entry in the provider list, as illustratively shown in Table I above. The matching entry may provide the delivery type and Destination ID associated with the Delivery Type, as described earlier.

Still referring to block 514, the healthcare survey module 108 may deliver a response 409 to the service provider computer 104. The response 409 may include the survey request and identification of the destination of the survey request (e.g., Destination Type, Destination ID). In an example embodiment of the invention, the destination of the survey request may designate a particular printer 184 or facsimile/other electronic device 186.

In block 516, the service provider computer 104 may deliver a message 410 with the survey request to the designated printer 184 or facsimile/other electronic device 186. In an example embodiment of the invention, the service provider computer 104 may direct the delivery of the message 410 with the survey request to the printer 184 or facsimile/other electronic device 186 via one or more networks, including the Internet, a cellular network or other wireless network, or a telephone network. As an example, the message 410 having the survey request may be delivered to the printer 184 or facsimile/other electronic device 186 without first being received by the physician/healthcare provider computer 102. For example, the message 410 may be delivered via a network (e.g., a cellular network, telephone network) using the destination ID corresponding to the printer 184 or facsimile/other electronic device 186. According to another example, the message 410 having the survey request may be delivered from the service provider computer 104 to the physician/healthcare provider computer 102 (e.g., as part of or distinct from the healthcare transaction acknowledgement 408), which in turn may deliver the message 410 having the survey request to the printer 184 or facsimile/other electronic device 186, which may be located at the physician/healthcare provider location. In an example embodiment of the invention, the message 410 may also provide a notification to the physician/healthcare provider computer 102 that the healthcare/informational content has been delivered to the printer 184 or facsimile/other electronic device 186. If the patient is the intended recipient of the survey request, then the patient may be provided with the survey request.

Figure 4B:
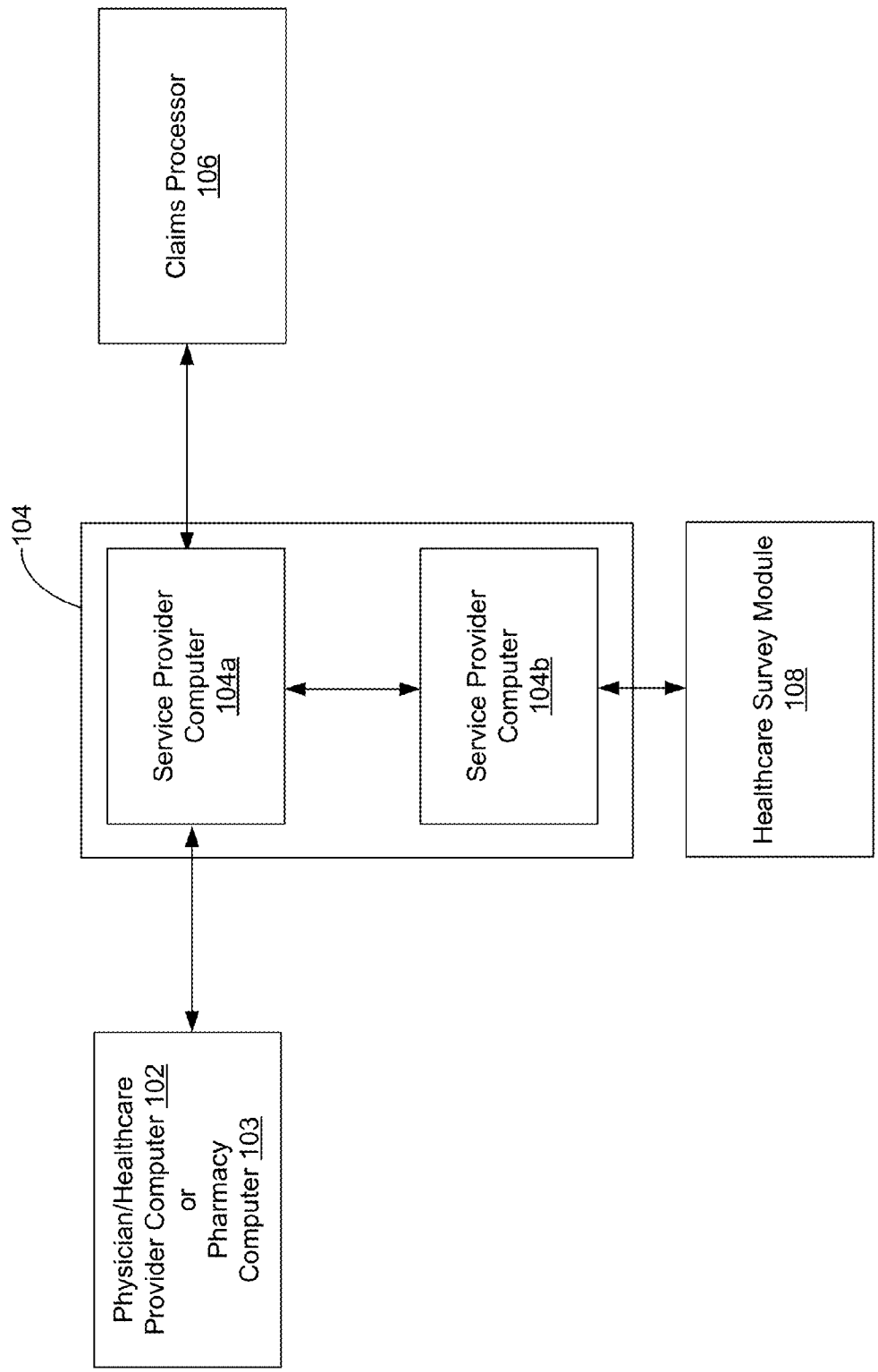

FIG. 4B illustrates a variation of the block diagram of FIG. 4A. As shown by FIG. 4B, the service provider computer 104 may be comprised of two or more distinct service provider computers 104*a* and 104*b* that are in communication with each other. Service provider computer 104*a* may be operative with the physician/healthcare provider computer 102, the pharmacy computer 103, and/or claims processor(s) 106 while service provider computer 104*b* may be operative with other physician/healthcare provider computers, pharmacy computers, and/or claims processors. However, service provider computer 104*b* may have a data processing arrangement with service provider computer 104*a*. Under the data processing agreement, the service provider computer 104*a* may be permitted to utilize or offer services accessible by the service provider computer 104*b*, including the services of the healthcare survey module 108. Accordingly, the services accessible by the service provider computer 104*b*, including the services of the healthcare survey module 108, may be available to the physician/healthcare provider computer 102 or pharmacy computer 103 via the service provider computers 104*a* and 104*b*.

It will also be appreciated that variations of FIG. 5 are also available without departing from example embodiments of the invention. According to a variation of FIG. 5, the service provider 104 may not automatically route the healthcare claim request to the claims processor 106, as provided in block 504. Instead, if block 510/512 determines that the particular healthcare claim transaction will not be selected for the survey, then the service provider 104 can proceed to perform the routing of block 504. However, if block 510/512 determines that the particular healthcare claim transaction is being selected for the survey, then the service provider 104 may deliver a denial response with a message to the physician/healthcare provider computer 102. The message may indicate that a survey request is being submitted to a printer 184 or facsimile/other electronic device 186, and should be delivered to a particular recipient. The message may further request the physician/healthcare provider computer 102 or pharmacy computer 103 resubmit the electronic prescription order transaction, perhaps with a particular override code, so that the service provider 104 can complete the healthcare claim transaction by routing the transaction to the claims processor 106 for adjudication or benefits determination. The above-described denial and resubmission process may increase the probability that the survey request is delivered to the intended recipient.

It will also be appreciated that according to other example embodiments of the invention, a service provider computer 104 may also direct a paper mailing of the survey request, including any survey questions, to a physical address of the intended recipient. The recipient can then mail the completed survey to a return location, or may otherwise use one of the other methods (e.g., network portal/website, call center, IVR system, etc.) described herein.

C. Survey Completion

Figure 6:
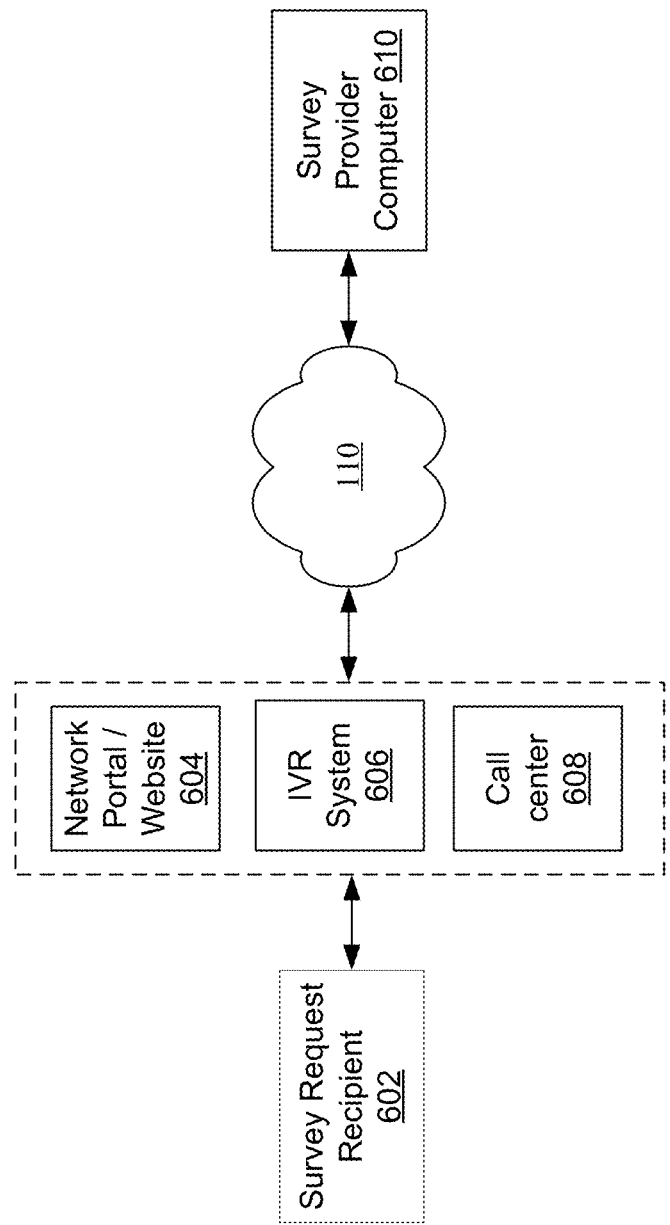
FIG. 6 illustrates an example block diagram for the completion of a survey by a survey request recipient, according to an example embodiment of the invention.
Figure 7:
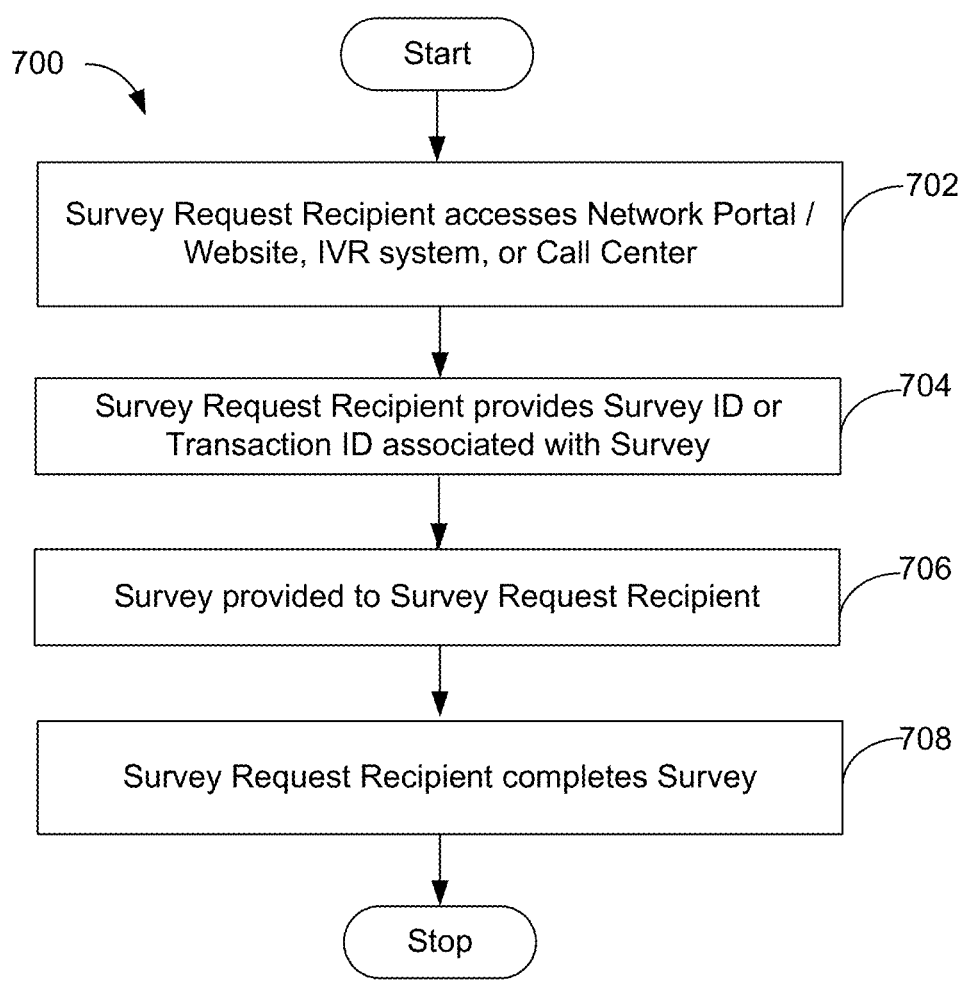
FIG. 7 illustrates an example flow diagram for the completion of a survey by a survey request recipient, according to an example embodiment of the invention.

FIG. 6 illustrates an example block diagram for the completion of a survey by a survey request recipient, according to an example embodiment of the invention. The operation of the block diagram of FIG. 6 will be discussed in conjunction with the example flow diagram 700 of FIG. 7. Referring to FIGS. 6 and 7, a survey request recipient 602 such as a patient, a healthcare provider (e.g., a physician, a pharmacist), or other individual may have received a survey request. For example, as described above, the survey request may have been received by a physician from a printer 184 or facsimile/other electronic device 186, and delivered to a patient at a physician location (e.g., doctor's office or hospital). As another example, the survey request may have been received by a pharmacist or pharmacy employee from a printer 184 or facsimile/other electronic device 186, and delivered to a patient in conjunction with a filled prescription order at a pharmacy location. On the other hand, the survey request may be targeted to the physician/healthcare provider or pharmacist/pharmacy employee, which themselves become the survey request recipient 602. As described herein, the survey request may include instructions regarding how to complete a survey, including an Internet address for accessing a survey portal/website or a telephone number for accessing a call center or an interactive voice response (IVR) system. In addition, the survey request may also include a survey ID or a transaction ID for identifying a particular survey request.

In block 702, a survey request recipient 602 may access and complete a survey by communicating with a survey provider 610 via a network portal/website 604, an interactive voice response (IVR) system 606, or a call center 608. For a network portal/website 604, the survey request recipient 602 may utilize an Internet browser-enabled computer to access an Internet address associated with a particular network portal/website. For an IVR system 606 or a call center 608, the survey request recipient may utilize a telephone and telephone number associated with the IVR system 606 or call center 608.

In block 704, the survey request recipient 602 provides the Survey ID or the Transaction ID to the network portal/website 604, the IVR system 606, or the call center 608. In block 706, the network portal/website 604, IVR system 606, or call center 608, may validate the received Survey ID or Transaction ID. The validation process may include a computer associated with the network portal/website 604, IVR system 606, or call center 608 transmitting a validation request with the Survey ID or Transaction ID to the survey provider computer 610 via network 110 for validation or identification of a survey. The survey provider computer 610 may be the service provider computer 104 and/or the healthcare survey module 108, according to an example embodiment of the invention. However, it will be appreciated that the survey provider computer 610 may also be a computer provided by or sponsored by another entity such as a marketing company or research company, according to an example embodiment of the invention.

In block 706, the network portal/website 604, IVR system 606, or call center 608 may identify a survey corresponding to the Survey ID or Transaction ID. For example, the network portal/website 604, IVR system 606, or call center 608 may receive the corresponding survey from the survey provider computer 610. The network portal/website 604, IVR system 606, or call center 608 may then present the survey, including one or more survey questions, to the survey request recipient 602. For the network portal/website 604, one or more forms or web pages having survey questions may be presented on an Internet browser of a computer of the survey request recipient 602. For the IVR system 606, a computerized system may verbally recite the survey questions to the survey request recipient 602 by telephone. For a call center 608, a human representative may read the survey questions to the survey request recipient 602 by telephone. FIG. 8 illustrates some example survey questions, according to an example embodiment of the invention.

In block 708, the survey request recipient 602 may complete the survey, either in whole or in part, by using the network portal/website 604, IVR system 606, or call center 608. For the network portal/website 604, one or more survey responses may be provided by the survey request recipient 602 by making one or more selections or entries into one or more forms or web pages associated with the network portal/website 604. For the IVR system 606, one or more survey responses may be provided, either verbally or by touch-tone telephone, by the survey request recipient 602 to the IVR system 606. For a call center 608, one or more survey responses may be verbally provided by the survey request recipient 602 to the call center 608 (e.g., a human representative records the survey responses on a computer at the call center 608).

The survey responses may ultimately be received by survey provider computer 610 and stored in a database, including database 182. Likewise, the database 182 may track which surveys associated with Survey IDs or Transaction IDs have completed, as well as which surveys associated with Survey IDs or Transaction IDS have not been completed. Indeed, an analysis of database 182 may indicate a response rate for survey requests. Other information associated with surveys or completed surveys may be stored in database 182 without departing from example embodiments of the invention.

It will also be appreciated that in some example embodiments of the invention, the recipient may have received a paper survey request (e.g., from a printer or facsimile as described above) that has the actual survey questions. For example, the recipient may be a patient or other individual that has received a paper survey request while at a physician/healthcare provider location. Likewise, the recipient may be a patient or other individual that has received a paper survey request while at a pharmacy location. The recipient may then complete the survey provided by the paper survey request. The completed survey is then provided to employee at the physician/healthcare provider location or pharmacy location, which is in turn faxed, mailed, or electronically delivered to an entity for storage and reporting, as described above.

The invention is described above with reference to block and flow diagrams of systems, methods, apparatuses, and/or computer program products according to example embodiments of the invention. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a general purpose computer, a special-purpose computer, a processor, or other programmable data processing apparatus to produce a particular machine, such that the instructions that execute on the computer, processor, or other programmable data processing apparatus create means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer usable medium having a computer readable program code or program instructions embodied therein, said computer readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

It will be appreciated that each of the memories and data storage devices described herein can store data and information for subsequent retrieval. The memories and databases can be in communication with each other and/or other databases, such as a centralized database, or other types of data storage devices. When needed, data or information stored in a memory or database may be transmitted to a centralized database capable of receiving data, information, or data records from more than one database or other data storage devices. In other embodiments, the databases shown can be integrated or distributed into any number of databases or other data storage devices.

It will also be appreciated that each of the I/O interfaces described herein may facilitate communication between a processor and various I/O devices, such as a keyboard, mouse, printer, microphone, speaker, monitor, bar code readers/scanners, RFID readers, and the like. Likewise, each of the network interfaces described herein may take any of a number of forms, such as a network interface card, a modem, a wireless network card, and the like.

It will further be appreciated that while the certain computers have been illustrated herein as a single computer or processor, the illustrated computers may actually be comprised of a group of computers or processors, according to an example embodiment of the invention.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method, comprising:
receiving, by a service provider system comprising one or more computers, a healthcare transaction comprising one of (i) a prescription order transaction to be routed by the service provider system from a physician/healthcare provider computer to a recipient pharmacy computer or (ii) a healthcare claim transaction to be routed by the service provider system from one of a physician/healthcare provider computer or a pharmacy computer to a claims processor computer, wherein the healthcare transaction identifies at least one or more of a drug for the patient, product for the patient, or service for a patient, a transaction response, a gender code of the patient, a date of birth of the patient, or a patient location information, and wherein the service provider system is configured to route the received healthcare transaction to a designated recipient computer;
determining, by the service provider system, that the received healthcare transaction is eligible for a survey based upon an analysis of one of more of the drug, product, service, transaction response, gender code, date of birth or patient location information identified in the received healthcare transaction;
selecting, by the service provider system, the eligible healthcare transaction for the survey based at least in part upon a predetermined selection process wherein the predetermined selection process is designated by a survey sponsor; and
delivering, by the service provider system, a survey request to a survey recipient associated with the selected healthcare transaction by electronic transmission to a facsimile or printer at a pharmacy location or a healthcare provider location without transmission through the physician/healthcare provider computer, the survey recipient being identified from information in the selected healthcare transaction, wherein the survey request includes at least a survey transaction identifier for identifying the survey.

2. The method of claim 1, wherein the survey recipient is the patient or a healthcare provider associated with the healthcare transaction.

3. The method of claim 1, wherein the survey recipient receives the survey by accessing a website, an IVR system, or a call center and provides the website, the IVR system, or the call center with the transaction identifier that identifies the survey.

4. The method of claim 1, wherein the printer is associated with a network ID, and wherein the survey request is transmitted in a message to the printer via a network, wherein the message specifies the network ID of the printer.

5. The method of claim 1, wherein the healthcare claim transaction comprises a medical claim request, wherein the medical claim request identifies at least the service for the patient.

6. A system, comprising:
at least one memory for storing computer-executable instructions; and at least one processor configured to access the memory and to execute the computer-executable instructions to:
receive a healthcare transaction comprising one of (i) a prescription order transaction to be routed from a physician/healthcare provider computer to a recipient pharmacy computer or (ii) a healthcare claim transaction to be routed from one of a physician/healthcare provider computer or a pharmacy computer to a claims processor computer, wherein the healthcare transaction identifies at least one or more of a drug for the patient, product for the patient, or service for a patient, a transaction response, a gender code of the patient, a date of birth of the patient, or a patient location information, and wherein the at least one processor is configured to route the received healthcare transaction to a designated recipient computer;
determine that the received healthcare transaction is eligible for a survey based upon an analysis of one of more of the drug, product, service, transaction response, gender code, date of birth or patient location information identified in the received healthcare transaction request;
select the eligible healthcare transaction for the survey based at least in part upon a predetermined selection process wherein the predetermined selection process is designated by a survey sponsor; and
deliver a survey request to a survey recipient associated with the selected healthcare transaction by electronic transmission to a facsimile or printer at a pharmacy location or a healthcare provider location without transmission through the physician/healthcare provider computer, the survey recipient being identified from information in the selected healthcare transaction, wherein the survey request includes at least a survey transaction identifier for identifying the survey.

7. The system of claim 6, wherein the survey recipient is the patient or a healthcare provider associated with the healthcare transaction.

8. The system of claim 6, wherein the survey recipient receives the survey by accessing a website, an IVR system, or a call center and provides the website, the IVR system, or the call center with the transaction identifier that identifies the survey.

9. The system of claim 6, wherein the printer is associated with a network ID, and wherein the survey request is transmitted in a message to the printer via a network, wherein the message specifies the network ID of the printer.

10. The system of claim 6, wherein the healthcare claim transaction comprises a medical claim request, wherein the medical claim request identifies at least the service for the patient.

* * * * *